(12) United States Patent
Kalanovic et al.

(10) Patent No.: US 8,211,050 B2
(45) Date of Patent: Jul. 3, 2012

(54) MEDICAL IMPLANT

(75) Inventors: Daniel Kalanovic, Stuttgart (DE);
Chi-Nghia Ho, Tubingen (DE);
Sebastian Schostek, Tubingen (DE);
Marc Oliver Schurr, Tubingen (DE)

(73) Assignee: Novineon Healthcare Technology Partners GmbH, Tubingen (DE)

( * ) Notice: Subject to any disclaimer, the term of this patent is extended or adjusted under 35 U.S.C. 154(b) by 1325 days.

(21) Appl. No.: 11/074,404

(22) Filed: Mar. 8, 2005

(65) Prior Publication Data
US 2005/0283107 A1 Dec. 22, 2005

(30) Foreign Application Priority Data
Mar. 9, 2004 (DE) .................... 10 2004 011 764

(51) Int. Cl.
*A61M 5/00* (2006.01)
*A61F 2/02* (2006.01)
*A61F 2/04* (2006.01)
*A61F 2/00* (2006.01)
*A61F 13/00* (2006.01)

(52) U.S. Cl. .......... 604/8; 604/9; 623/11.11; 623/23.64; 600/37

(58) Field of Classification Search ............... 604/8, 9; 623/11.11, 23.64; 600/37
See application file for complete search history.

(56) References Cited

U.S. PATENT DOCUMENTS

| 4,501,264 | A | * | 2/1985 | Rockey | 128/898 |
|---|---|---|---|---|---|
| 4,846,836 | A | * | 7/1989 | Reich | 623/23.68 |
| 5,246,456 | A | * | 9/1993 | Wilkinson | 623/23.65 |
| 5,306,300 | A | | 4/1994 | Berry | |
| 5,314,473 | A | * | 5/1994 | Godin | 623/23.68 |
| 5,820,584 | A | * | 10/1998 | Crabb | 604/500 |
| 5,861,036 | A | | 1/1999 | Godin | |
| 6,675,809 | B2 | * | 1/2004 | Stack et al. | 128/898 |
| 7,510,559 | B2 | * | 3/2009 | Deem et al. | 606/151 |
| 2004/0024386 | A1 | * | 2/2004 | Deem et al. | 606/1 |
| 2004/0039452 | A1 | * | 2/2004 | Bessler | 623/23.65 |
| 2004/0138760 | A1 | * | 7/2004 | Schurr | 623/23.65 |
| 2005/0197714 | A1 | * | 9/2005 | Sayet | 623/23.65 |

FOREIGN PATENT DOCUMENTS
WO WO 02/096325 12/2002

* cited by examiner

*Primary Examiner* — Leslie Deak
*Assistant Examiner* — Adam Marcetich
(74) *Attorney, Agent, or Firm* — Robert L. Epstein; Epstein Drangel LLP (57) ABSTRACT

The medical implant for treating pathological obesity is adapted to modify and, as an alternative, to bypass the natural food passage in the digestive tract. The implant permits an adjustable bypassing of food into the small intestine and/or into the stomach (natural digestive path). Since the ratio of this bypass is adjustable in the course of the treatment by the physician, e.g. with the aid of an endoscope, for the first time a balance between the therapeutic effect and the side-effects can be adapted individually to each patient by the use of the implant. The implant has a hollow body with first and a second tubular end portions and at least one third lateral opening having a hose-like extension. The individual at least partly closable hose-like extensions differ in their ability to allow the passage of food into the stomach. Closing individual hose-like extensions at least partially by means of an endoscope leads to an individually adjustable distribution of food between the stomach and the small-intestine loop.

8 Claims, 14 Drawing Sheets

MEDICAL IMPLANT

This application claims the priority of German patent application no. 10 2004 011 764.0, filed Mar. 9, 2004.

DESCRIPTION

The present invention relates to a device for treating pathological obesity and especially to a medical implant which is adapted to modify and, as an alternative, to bypass the natural food passage in the digestive tract. In contrast to purely surgical methods of food bypassing, the properties of the present implant permit an adjustable bypassing of food into the small intestine and/or into the stomach (natural digestive path). Since the ratio of this bypass is adjustable in the course of the treatment by the physician e.g. with the aid of an endoscope, for the first time a balance between the therapeutic effect (loss of weight) and side-effects (excessive malabsorption) can be adapted individually to each patient by the use of the implant.

Today massive overweight is defined by the Body Mass Index (BMI), as it is called. It results from the body weight in kilograms (kg) divided by the body size square in meters (m). A BMI of more than 40 corresponds to massive overweight. Massive overweight of human beings has a number of consequences of health such as cardiovascular diseases, diabetes and damage of the locomotor system. In extreme forms of obesity despite making every effort usually only a reduction by several kilograms is achieved which is hardly noticeable. In these extreme cases the indication for surgical therapy may be given. In a surgical therapy of massive overweight nowadays operations, among which the "gastric banding" and the "gastric bypass" are prevailing, are carried out.

Gastric Banding

In the case of this operation the entrance area of the stomach is constricted by an implanted synthetic belt whereby a stomach pouch is formed which is communicated with the other stomach area only via a small outlet. This operation may result in the fact, however, that after the operation the patient eats more high-caloric food or that the constricted stomach pouch bulges and expands so that a certain re-increase in weight is probable. Moreover it is possible that the silicone belt slips out of place or breaks into the stomach.

Gastric Bypass

In the case of this operation a stomach pouch is surgically cut off with the aid of clip suture devices in the entrance area of the stomach. The stomach of the patient is completely severed and the stomach pouch formed is no longer connected to the other stomach area but to the anastomosed small-intestine loop which is lifted and fixed to the stomach pouch. The food passes the esophagus, the stomach pouch and then flows into the small-intestine loop, wherein the residual stomach and the duodenum are excluded from the food passage but also from endoscopic examinations. The gastric bypass results in more weight reduction than the gastric banding.

The operation is deemed to be irreversible, however, which is disadvantageous in the case of later complications such as, for instance, consequences of malabsorption which are difficult to control. Furthermore there is a risk that sutures at the clip suture devices become leaky, thus making a further operation necessary. A gastroscopic examination of the cut off stomach and duodenum is no more possible after the operation, either.

It is the object of the invention to provide a device for the treatment of pathological obesity which fights obesity in the long run, does not put as much strain on the patient as present methods and permits a reversible operation at the patients.

Previous hollow implants for the treatment of pathological obesity (patents No WO 88 05671 A, U.S. Pat. No. 4,315,509 A, U.S. Pat. No. 5,306,300) describe a structure which is to absorb the food passing through the esophagus and continue the natural gastrointestinal transport path. Inside these implants the food is to be separated from the digestive mechanisms and the nutrient absorption is to be impaired in this way.

In contrast to the aforementioned implant concepts, the object is achieved by the described device according to claim 1 on the one hand by a bypass of food taken in through a provided opening into the small intestine. On the other hand, the implant permits a gradually adjustable food passage into the completely retained stomach and thus a scaleable natural gastrointestinal transport path. Advantageous further developments are explained in the dependent claims.

The device is a medical implant comprising a hollow body adapted to be implanted in the stomach of a patient for a temporary intake of food including a first tubular end portion, a second tubular end portion and at least one third lateral opening between the first and second tubular end portions. The first tubular end portion is dimensioned so that it is adapted to be tightly fitted into the esophagus of the patient. The second tubular end portion is dimensioned so that it is adapted to be tightly connected with the small-intestine loop of the patient. The third lateral opening has a hose-like extension and establishes a communication between the hollow body and the interior of the stomach so that part of the food can pass from the hollow body into the stomach. Moreover the endoscopic inspection of the stomach is permitted through a lateral opening.

According to an advantageous further development, the implant includes fixing means at the first and second tubular end portion for fixing the end portions to parts of an organ of the patient.

According to another advantageous further development, the implant shows a hollow central member between the first and second end portions which is bulged relative to the end portions and is communicated with the same. This central portion of the implant absorbs the substances passing through the first tubular end portion and selectively guides them either through the second tubular end portion to the loop of the small intestine or through a lateral opening into the interior of the stomach.

According to another advantageous further development, the hollow central member of the implant consists of a flexible material or a flexible structure so as to absorb, on the one hand, the substances passed via the first tubular end portion without difficulties and, on the other hand, to ensure the mechanical incorporation in the human anatomy.

According to another advantageous further development, at least one lateral opening is located in the area of the hollow central member. From the hollow central member substances or medical instruments can pass via this lateral opening directly into the interior of the stomach.

In accordance with another advantageous further development, the hose-like extension of the lateral opening consists of an easily deformable material or an easily deformable structure so that the hose-like extension can be easily turned inward for the purpose of closing and can be equipped with a mechanical closing device.

According to another advantageous further development the hose-like extension of the lateral opening has a structure which facilitates gripping the hose-like extension by medical instruments. In the event of an endoscopic operation the hose-like extension of a lateral opening can thus be gripped more easily by mechanical instruments, such as e.g. forceps, and consequently be drawn into the interior of the hollow body for the purpose of closing the lateral opening.

According to a further advantageous development, the hose-like extension of a lateral opening is adapted to be at least partly closed. This can be performed by disposing a mechanical device at the hose-like extension which is turned into the hollow body. In this way the ratio of the passage of substances into the stomach and into the loop of the small intestine can be adjusted.

The invention will be illustrated along with its advantages by the following description of the embodiment together with the enclosed drawings.

Figure 1:
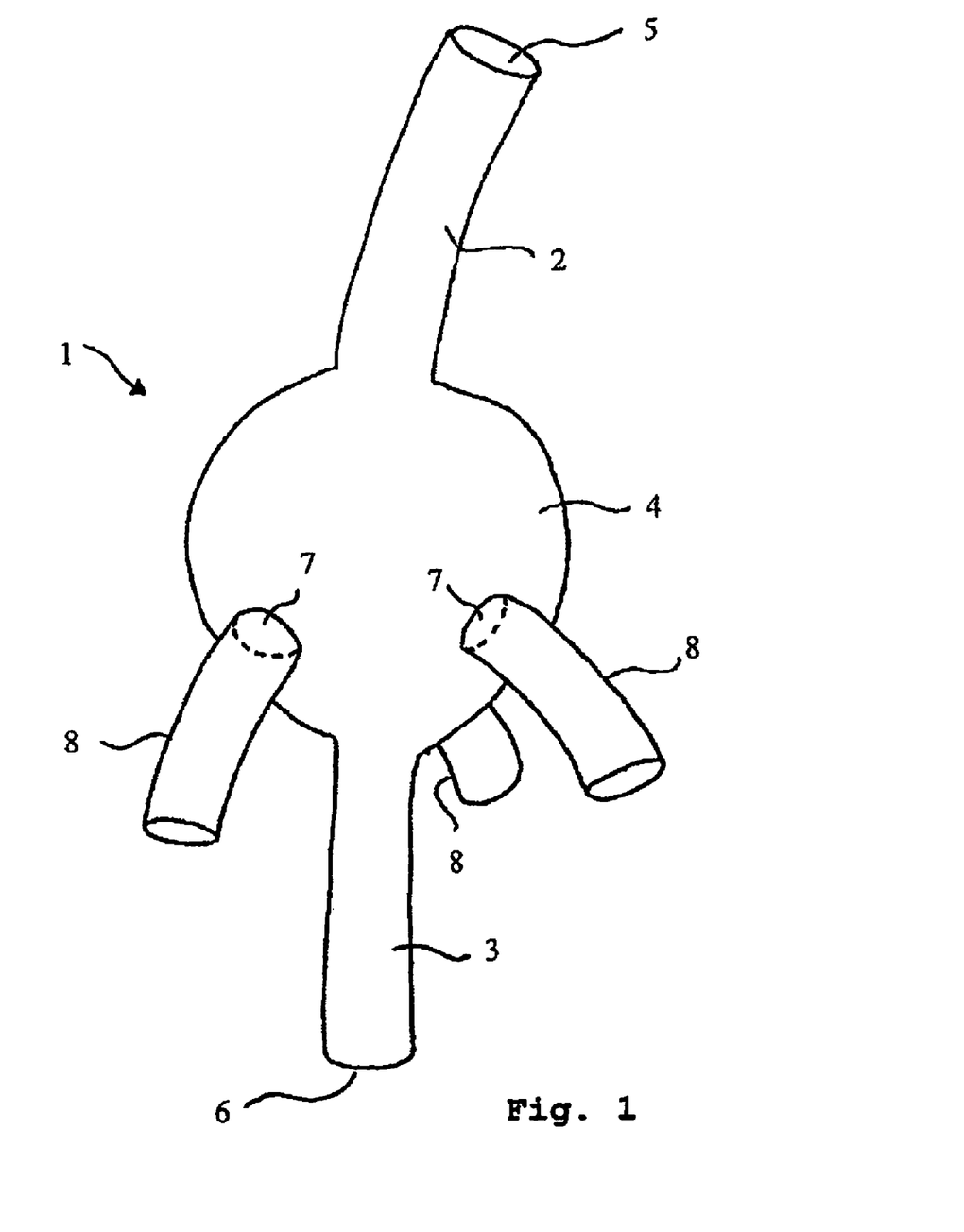
FIG. 1 shows an embodiment of the present invention.

In FIG. 1 a medical implant for treating pathological obesity is shown according to an embodiment of the present invention. This implant is a flexible hollow body 1. The hollow body 1 includes a first tubular end portion 2 and a second tubular end portion 3. The first tubular end portion is dimensioned such that it is adapted to be fitted in the esophagus of the patient. The second tubular end portion 3 is dimensioned such that it is adapted to be fitted in the loop of the small intestine of the patient.

Each of the first and second tubular end portions 2, 3 has a first opening 5 and a second opening 6, respectively. At the first and second tubular end portions 2, 3 fixing devices (not shown) are provided by which the end portions 2, 3 can be fixed to parts of an organ of the patient.

The hollow body 1 includes a hollow central member 4 which is bulged relative to the first and second end portions 2, 3 and is communicated with the first and second end portions 2, 3. This central portion 4 defines the later artificial stomach volume of the patient. Since the central member 4 is flexible, the artificial stomach volume can expand to a certain extent depending on the filling ratio of the central member 4. The central member 4 has three lateral openings 7 which are annularly located level with each other at regular spaces at the central member 4. Each of these lateral openings 7 includes a hose-like extension 8.

Figure 2:
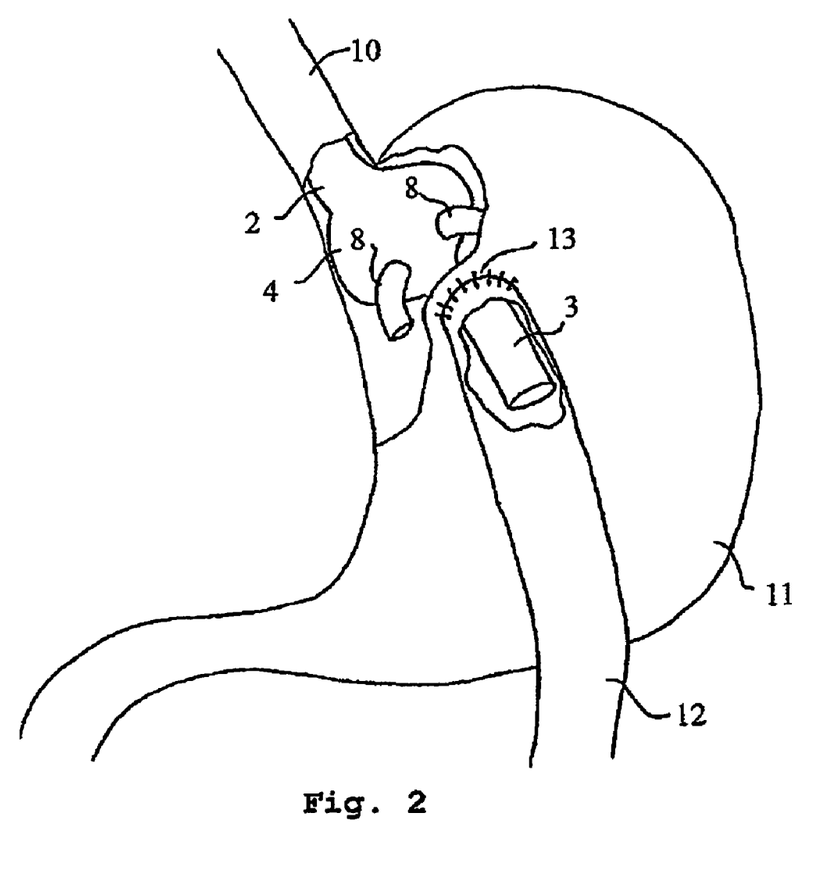
FIG. 2 shows the embodiment of the present invention while being implanted in the stomach of a patient.

FIG. 2 shows in which way the medical implant for the treatment of pathological obesity according to the embodiment of the present invention is implanted in the stomach.

Here the arrangement of the implant in the stomach is clearly evident. The first tubular end portion 2 is fitted into the esophagus 10, while the second tubular end portion 3 is fitted into a discharging small-intestine loop 12. The small-intestine loop 12 has been circularly clipped to the stomach wall in advance by e.g. clip suture devices 13 after an appropriate perforation in the stomach wall was provided at this location. In this way a bypass which is capable of completely bypassing the stomach 11 and the duodenum (not shown) is realized by the implant between the esophagus 10 and the small intestine 12.

The hose-like extensions 8 of the lateral openings 7 point in different directions. It is provided that individual hose-like extensions 8 permit the food passage into the stomach 11 to different extents. Thus an individually adjustable food distribution between the stomach 11 and the small-intestine loop 12 is resulting.

The food passes from the esophagus 10 through the first opening 5 and the first tubular end portion 2 into the central member 4. From the central member 4 the food can either pass through the second tubular end portion 3 and through the second opening 6 into the small-intestine loop 12, or else through a lateral opening 7 and a hose-like extension 8 into the stomach 11. The volume ratio between the food transmitted to the small-intestine loop 12 and the food transmitted to the stomach 11 determines the therapeutic effect of the implant. This ratio is adjustable by closing one or more lateral openings 7.

Figure 3:
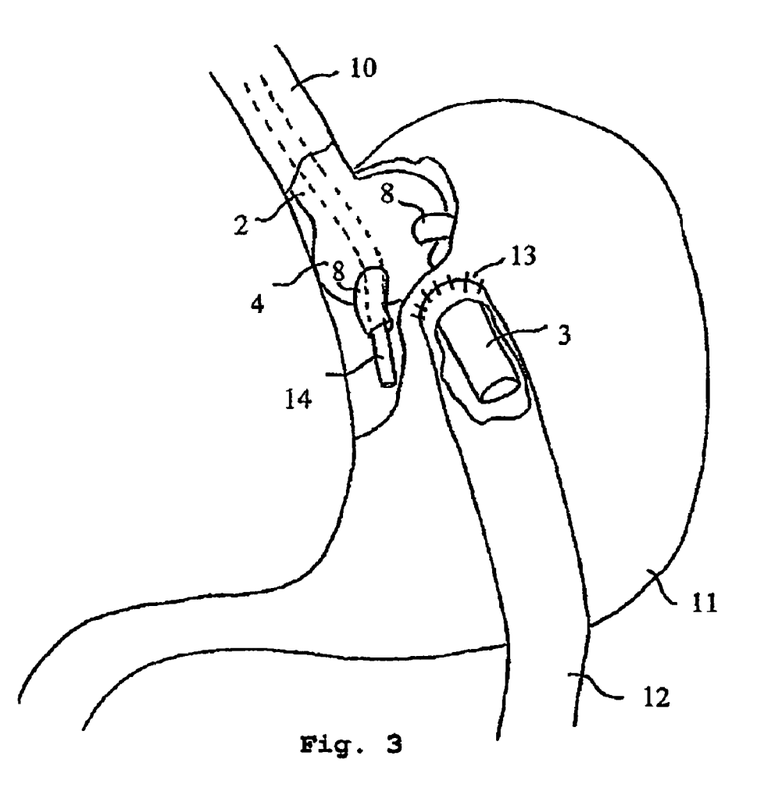

FIG. 3 shows the gastroscopic inspection of the stomach with the aid of an endoscope 14.

Figure 4:
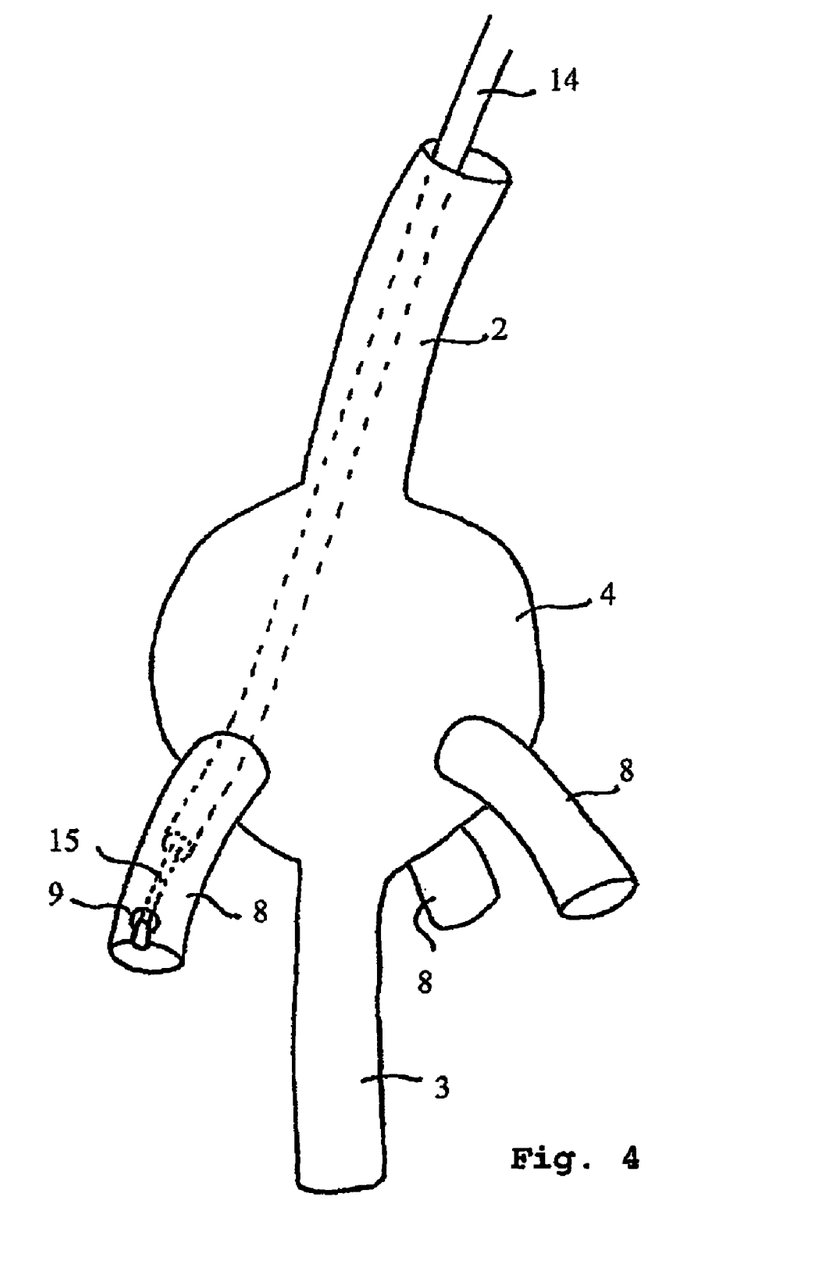

FIG. 4 shows the gripping of a hose-like extension 8 of a lateral opening 7. The structure 9 disposed at the tip of the hose-like extension 8 enables the hose-like extension 8 to be easily gripped by endoscopic forceps 15. This process can be executed using an endoscope 14.

Figure 5:
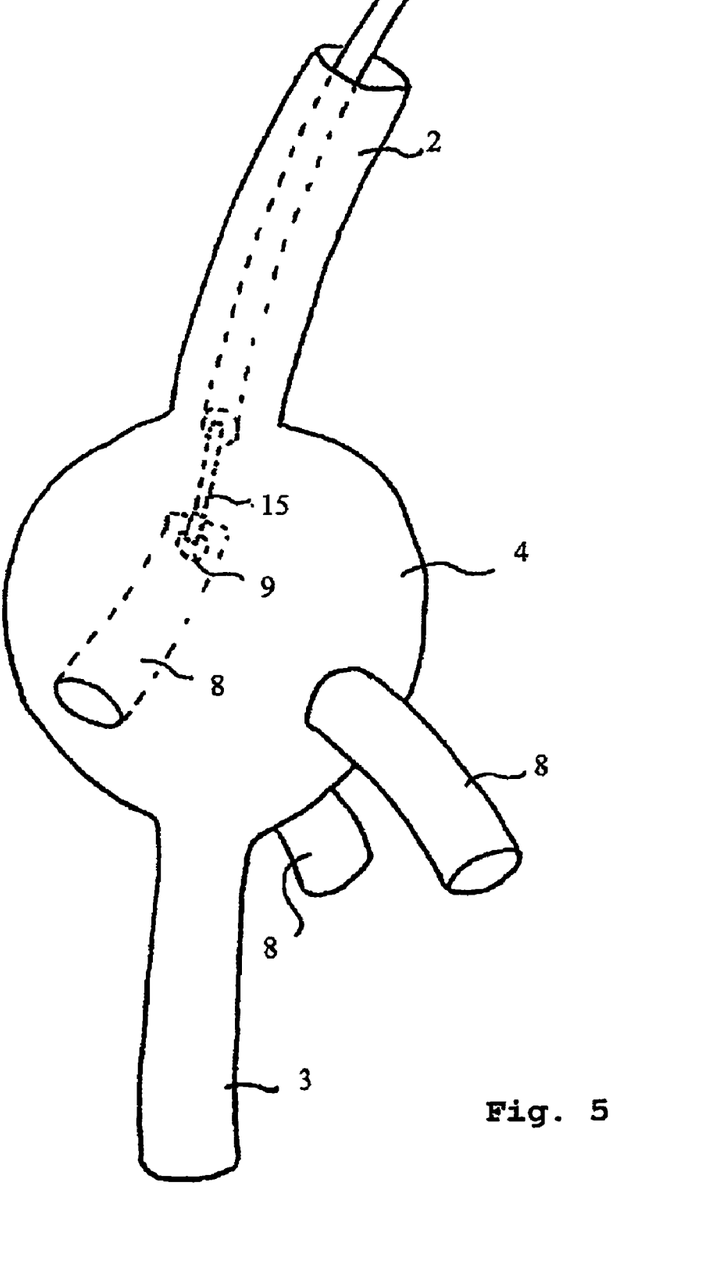

FIG. 5 shows the turning in of a hose-like extension 8 with the aid of the endoscopic forceps 15. This process can be executed using an endoscope 14.

Figure 6:
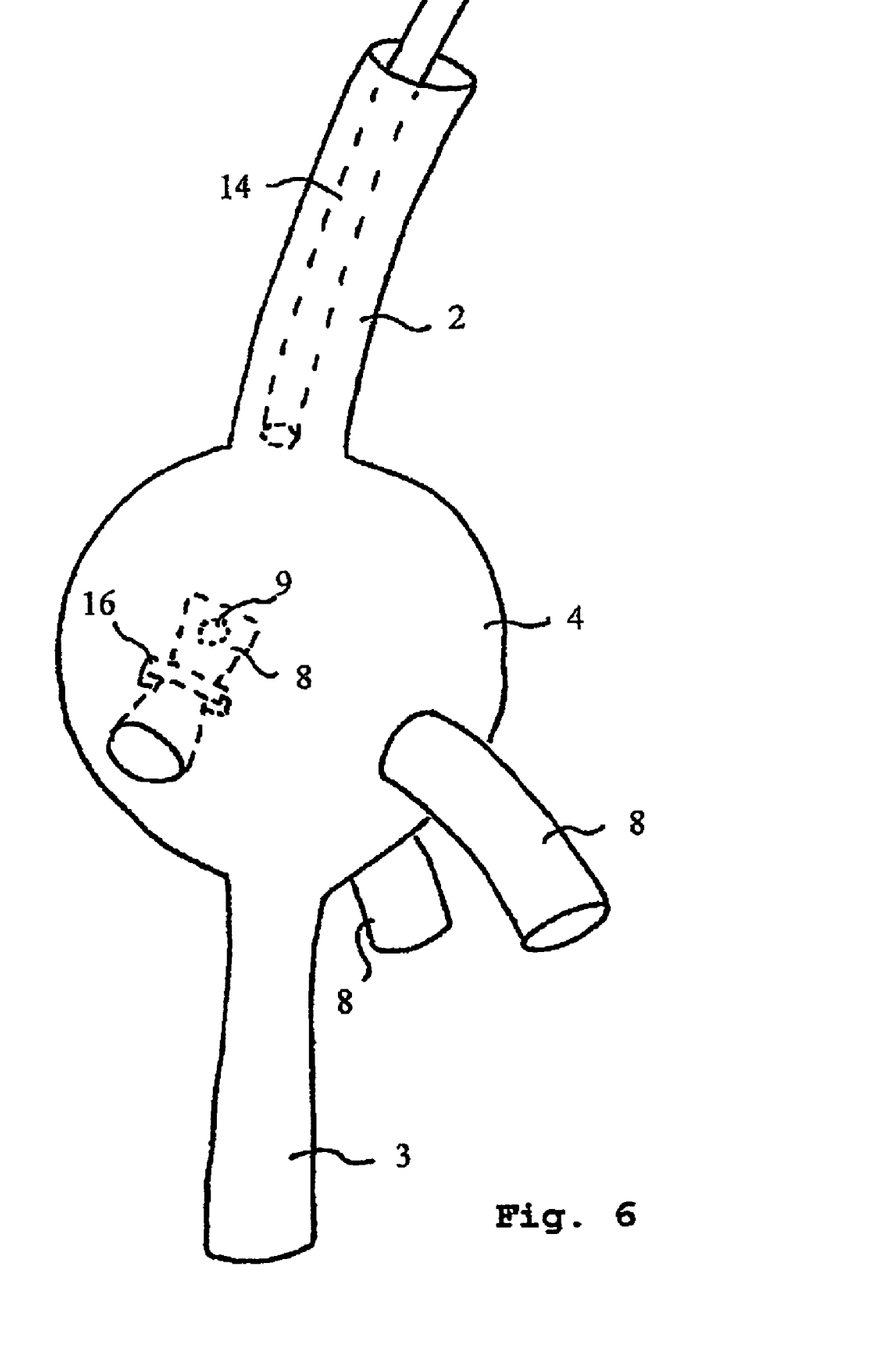

FIG. 6 shows the closing of a hose-like extension 8 which has been turned in. For this purpose a mechanical device 16, such as e.g. a clip or a rubber belt, is applied to the turned-in hose-like extension. This process can be executed using an endoscope 14.

Figures 7, 7A:
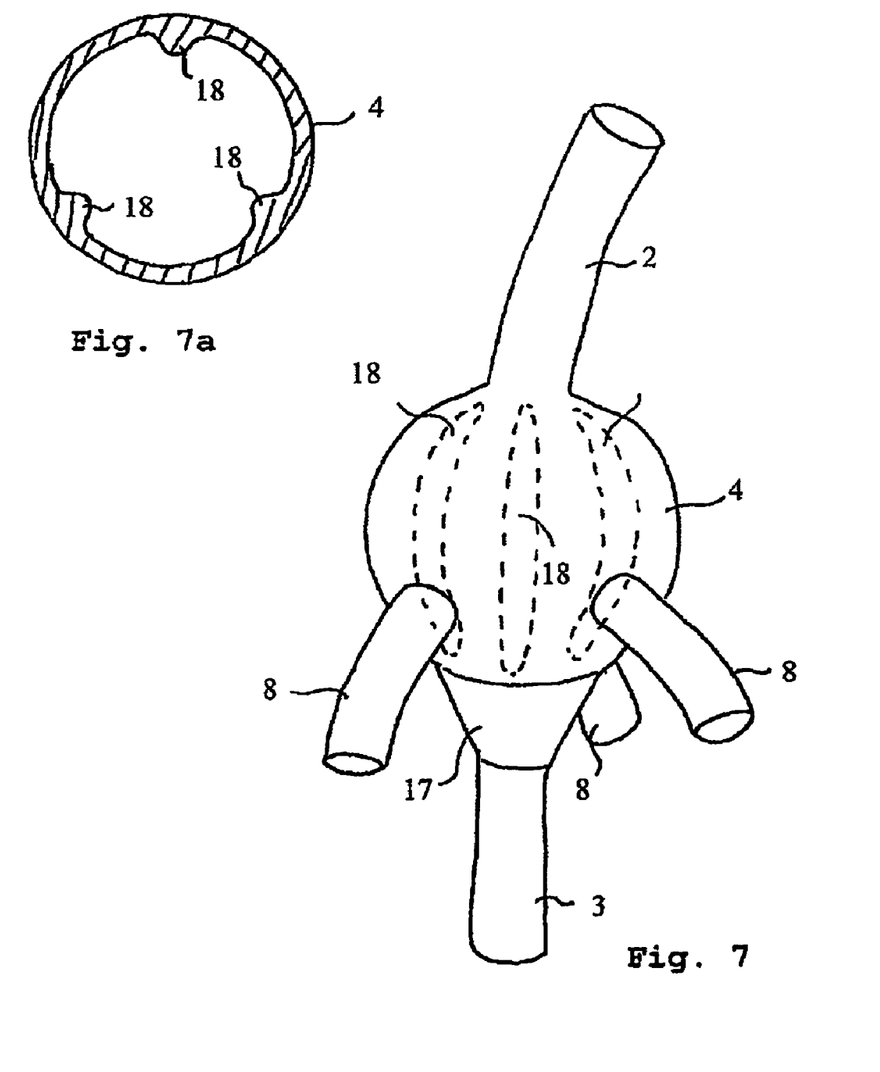

FIG. 7 shows the implant in an advantageous embodiment. The second tubular end portion 3 has a mechanically fixed funnel-shaped structure. FIG. 7a shows the hollow body of the implant in a sectional view. The wall of the hollow body has a longitudinal structure 18 which is to prevent the wall of the hollow body from bending in parallel to the axial plane. Thus folds formed transversely to the direction of flow of substances are to be prevented from occurring in the wall of the hollow body so as to permit a smooth passage through the implant. Moreover substances are guided in the hollow body from the first end portion in the direction of the second end portion.

FIGS. 8a through 8f show different variants of the lateral opening 7.

Figure 8A:
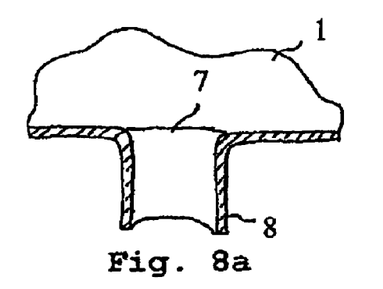

FIG. 8a shows a lateral opening 7 in a simple variant.

Figure 8B:
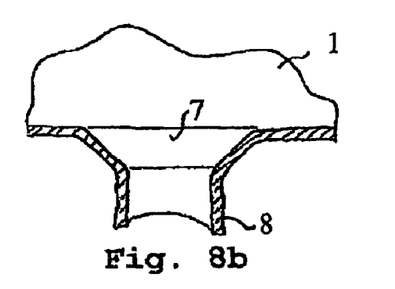

FIG. 8b shows a lateral opening 7 including a funnel-shaped end portion 19 at the transition between the hose-like extension 8 and the hollow body 1.

Figure 8C:
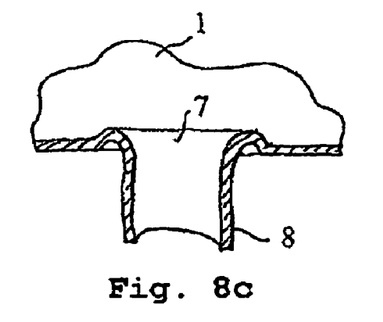

FIG. 8c shows a lateral opening 7 including a fold 20 at the transition between the hose-like extension 8 and the hollow body 1.

Figure 8D:
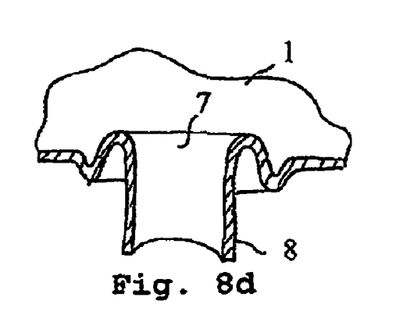

FIG. 8d shows a lateral opening 7 including a double fold 21 at the transition between the hose-like extension 8 and the hollow body 1.

Figure 8E:
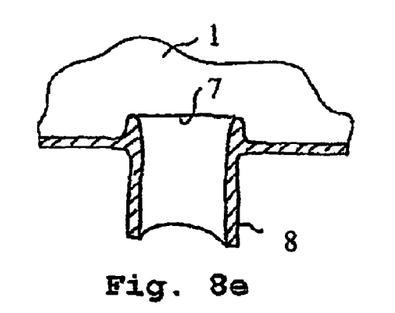

FIG. 8e shows a lateral opening 7 including a bulging 22 at the transition between the hose-like extension 8 and the hollow body 1 in parallel to the hose-like extension.

Figure 8F:
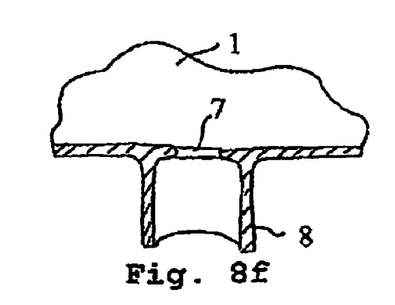

FIG. 8f shows a lateral opening 7 including a bulging 23 at the transition between the hose-like extension 8 and the hollow body 1 perpendicular to the hose-like extension.

Figure 8G:
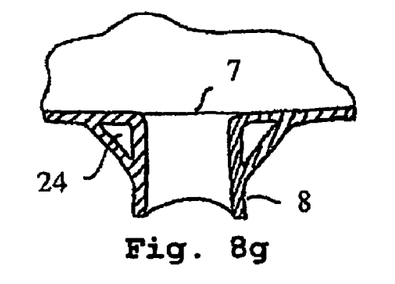

FIG. 8g shows a lateral opening 7 including a hollow space 24 at the transition between the hose-like extension 8 and the hollow body 1.

FIGS. 9a through 9g show different variants of the hose-like extension.

Figure 9A:
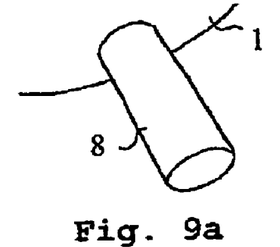

FIG. 9a shows a hose-like extension 8 which has a constant cross-section over its length.

Figure 9B:
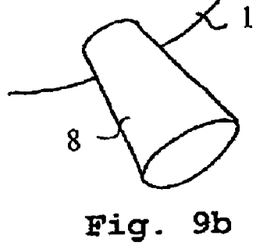
Figure 9C:
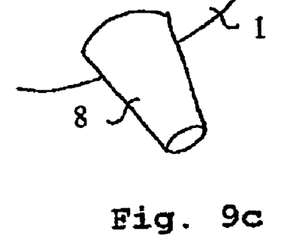

FIGS. 9b and 9c show a hose-like extension 8 which is funnel-shaped.

Figure 9D:
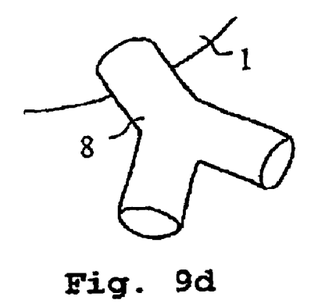
Figure 9E:
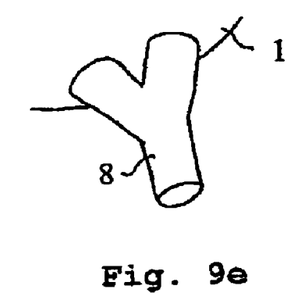

FIGS. 9d and 9e show a hose-like extension 8 which has a branching.

Figure 9F:
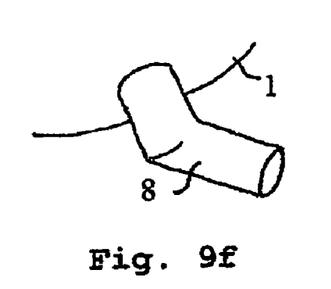

FIG. 9f shows a hose-like extension 8 which has a kink.

Figure 9G:
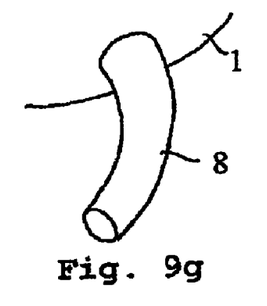

FIG. 9g shows a hose-like extension 8 which has a bend.

FIGS. 10a through 10h show different variants of the cross-section of the hose-like extension 8.

Figure 10A:
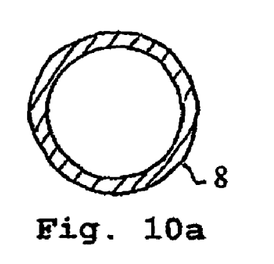

FIG. 10a shows a circular cross-section of the hose-like extension 8.

Figure 10B:
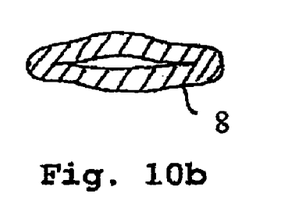

FIG. 10b shows a slit-like cross-section of the hose-like extension 8.

Figure 10C:
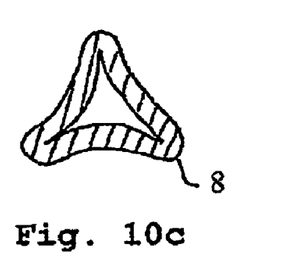
Figure 10D:
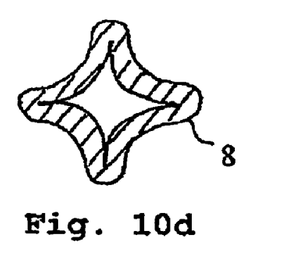

FIGS. 10c and 10d show variants of a star-shaped cross-section of the hose-like extension 8.

Figure 10E:
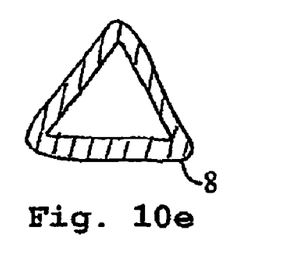
Figure 10F:
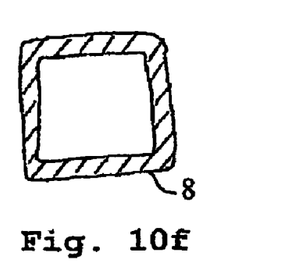

FIGS. 10e and 10f show variants of an angular cross-section of the hose-like extension 8.

Figure 10G:
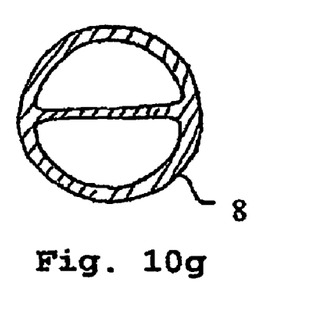
Figure 10H:
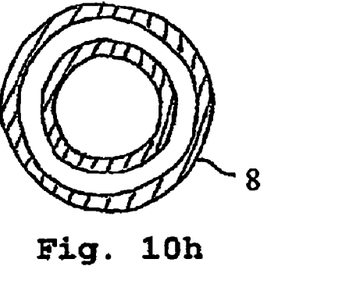

FIGS. 10g and 10h show variants of a segmented cross-section of the hose-like extension 8.

FIGS. 11a through 11e show different variants of a structure with the aid of which the gripping of the hose-like extension by a mechanical instrument is facilitated.

Figure 11A:
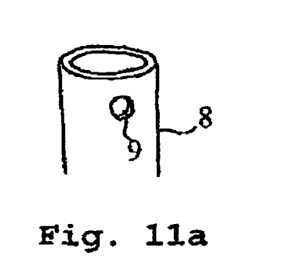

FIG. 11a shows a variant of the structure 9 having an opening in the hose-like extension 8.

Figure 11B:
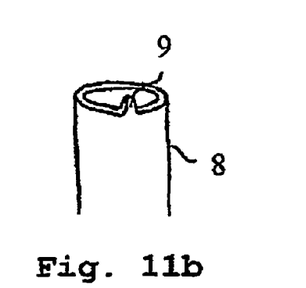

FIG. 11b shows a variant of the structure 9 having a bulge on the front of the hose-like extension.

Figure 11C:
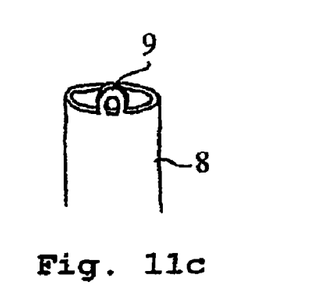

FIG. 11c shows a variant of the structure 9 having a bracket on the front of the hose-like extension.

Figure 11D:
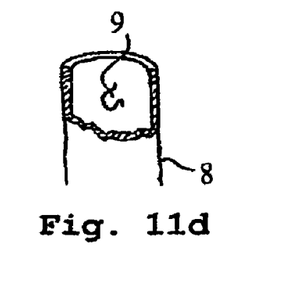

FIG. 11d shows a variant of the structure 9 having a bulge on the inside of the hose-like extension.

Figure 11E:
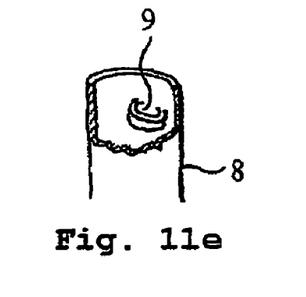

FIG. 11e shows a variant of the structure 9 having a bracket on the inside of the hose-like extension.

Figure 12A:
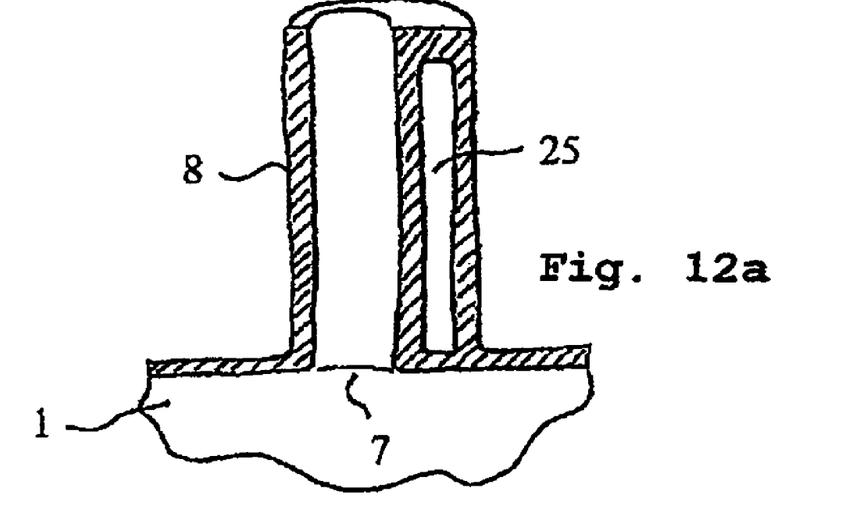
Figure 12B:
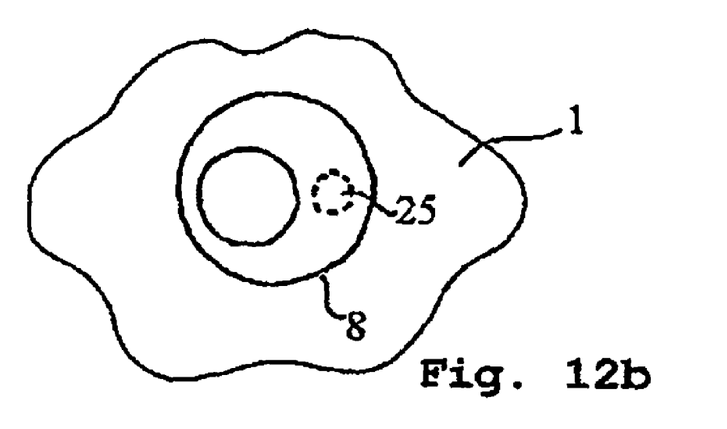

FIG. 12a and FIG. 12b show the longitudinal hollow space 25 in the outer wall of the hose-like extension 8 in a side view (FIG. 12a) and in a top view (FIG. 12b). By filling the longitudinal hollow space with a medium or by introducing a foreign body the stiffness of the hose-like extension 8 can be influenced, whereby in turn the passage of substances through the respective lateral opening 7 can be varied.

Figure 13A:
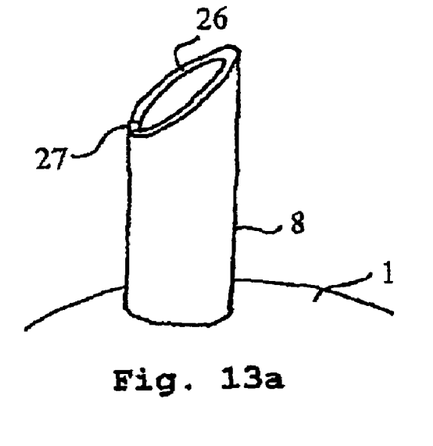
Figure 13B:
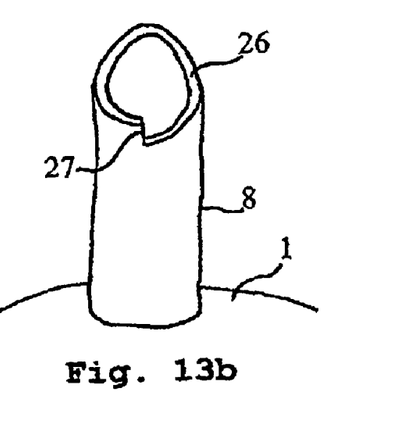

FIGS. 13a and 13b show a hose-like extension 8 which has an inclined front 26 and a step 27 in the inclined front 26 in a side view (FIG. 13a) and in a front view (FIG. 13b). This design is intended to obtain a preferred direction and/or to prevent a blocking when turning in the hose-like extension.

Figure 14A:
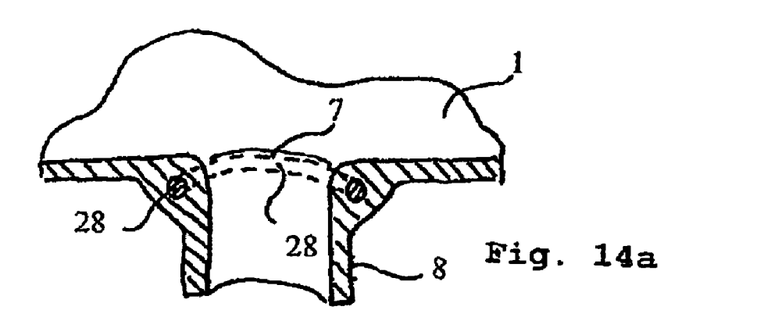
Figure 14B:
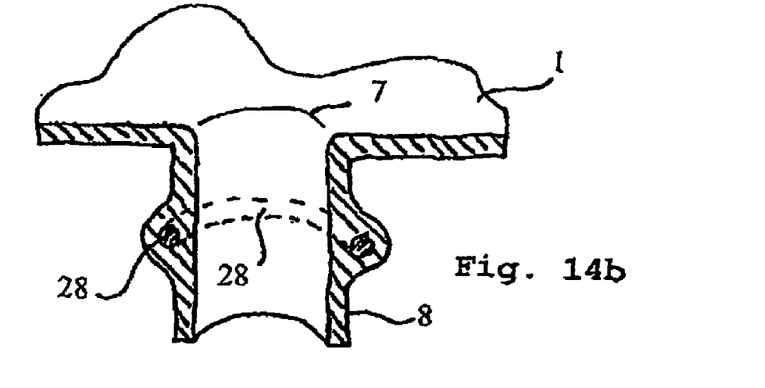
Figure 14C:
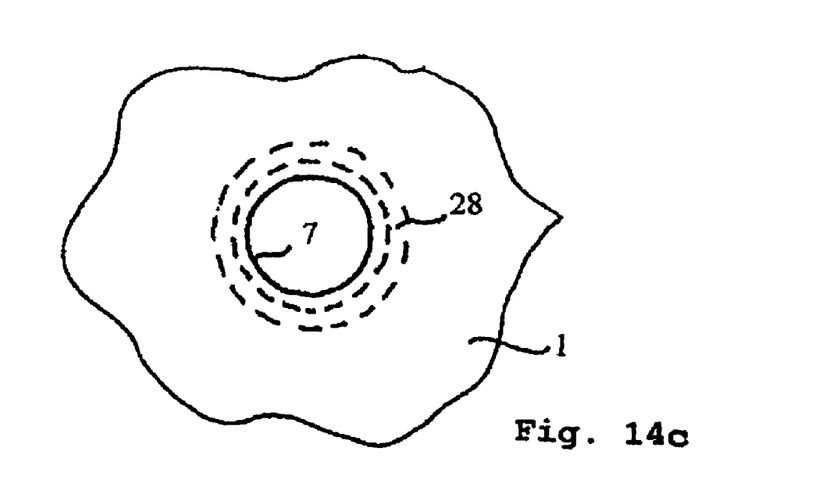

FIGS. 14a through 14c show two variations of an internal closing mechanism for the at least partial closing of a lateral opening 7 and/or a hose-like extension 8 in a sectional side view (FIGS. 14a and 14b) as well as in a top view (FIG. 14c). For this purpose a device 28, e.g. a loop, whose diameter can be varied by external manipulation is introduced in the wall of the hollow body 1 or of the hose-like extension 8.

The implant in accordance with the present invention has the following advantages. The entire operation can be performed by minimally invasive operating methods, whereby the discomforts and risks for the patient are minimized. In general the implant can be removed from the patient again, whereby the operation is reversible by simple means in contrast to the gastric bypass. Consequently, complications occurring later can be eliminated by removing the implant. It is another advantage with respect to the gastric bypass that delimiting a gastric pouch by clip suture devices is not necessary. Thus no sutures which might entail later complications are made at this location by the implant.

Moreover a considerable loss of weight is possible, because the food passes the stomach and the duodenum only partly, digestive juices from the gallbladder and the pancreas only later can get into contact with the food and moreover the upper small intestine area is bypassed. In this way the active intestine surface is strongly reduced and the nutrient absorption is massively diminished. On the other hand, in contrast to the gastric bypass the latter therapeutic effect can be scaled at the implant by a postoperative adjustment. So undesired side-effects occurring e.g. by excessive malabsorption can be reduced.

In addition, in contrast to the previous gastric bypass method an access to the stomach is maintained so that this area continues to be available for gastroscopic examinations.

The invention claimed is:

1. A medical implant consisting of a hollow body to be implanted into the stomach of a patient comprising a first tubular end portion forming a food inlet opening and dimensioned so that it is fittable into the esophagus of the patient, a second tubular end portion forming a food outlet opening and dimensioned so that it is tightly connectable to a small-intestine loop of the patient and a middle portion forming an artificial stomach volume having a wall defining an interior passage connecting the inlet and outlet openings of the first and second tubular end portions characterised in that the middle portion wall has an opening and a hose-like member extending from said wall opening, said hose-like member terminating within the stomach volume of the patient, at a point downstream of said wall opening, wherein food can bypass a section of said interior passage by moving through said hose-like member from said interior passage into the stomach volume of the patient.

2. A medical implant according to claim 1, characterized in that the hose-like member has at least one kink.

3. A medical implant according to claim 1, characterized in that the hose-like member has a circular cross-section.

4. A medical implant according to claim 1, characterized in that the hose-like member has at least one structure which facilitates gripping by a mechanical instrument.

5. A medical implant according to claim 1, characterized in that the hose-like member has at least one structure which facilitates gripping by a mechanical instrument, said structure being a bracket on the inside of the hose-like member.

6. A medical implant according to claim 1, characterized in that the lateral opening has a hollow space.

7. A medical implant according to claim 6, characterized in that a medium is introducible into the hollow space.

8. A medical implant according to claim 6, characterized in that the diameter of the lateral opening is varied by introducing a medium into the hollow space.

* * * * *